United States Patent [19]

Sakimae et al.

[11] Patent Number: 5,149,855
[45] Date of Patent: Sep. 22, 1992

[54] PROCESS FOR RACEMIZING OPTICALLY ACTIVE CARBOXYLIC ACID ESTERS

[75] Inventors: Akihiro Sakimae; Eiji Ozaki; Kanehiko Enomoto; Ryozo Numazawa; Yoshimasa Kobayashi, all of Otake, Japan

[73] Assignee: Mitsubishi Rayon Co., Ltd., Tokyo, Japan

[21] Appl. No.: 627,779

[22] Filed: Dec. 14, 1990

[30] Foreign Application Priority Data

Dec. 26, 1989 [JP] Japan .................................. 1-336893

[51] Int. Cl.$^5$ ............................................. C07C 327/00
[52] U.S. Cl. ........................................ 558/255; 558/257
[58] Field of Search ................................. 558/257, 255

[56] References Cited

U.S. PATENT DOCUMENTS 4,411,836 10/1983 Ohashi et al. ......................... 558/257
4,917,821 4/1990 Mori et al. ............................. 558/257

FOREIGN PATENT DOCUMENTS 3424440 1/1985 Fed. Rep. of Germany ...... 558/257

*Primary Examiner*—Mary C. Lee
*Assistant Examiner*—Robert C. Whittenbaugh
*Attorney, Agent, or Firm*—Oblon, Spivak, McClelland, Maier & Neustadt

[57] ABSTRACT

Process for racemizing an optically active carboxylic acid ester of the formula (1):

$$R_1-\overset{O}{\overset{\|}{C}}S-(CH_2)_n-\overset{R_2}{\overset{|}{C}}H\overset{O}{\overset{\|}{C}}O-R_3 \quad (1)$$

wherein $R_1$ is alkyl, aralkyl or aryl, $R_2$ and $R_3$ independently are alkyl, and n is 1 or 2, which comprises contacting the compound of the formula (1) with an amine compound.

3 Claims, No Drawings

PROCESS FOR RACEMIZING OPTICALLY ACTIVE CARBOXYLIC ACID ESTERS

FIELD OF THE INVENTION

The present invention relates to a process for racemizing an optically active carboxylic acid ester.

BACKGROUND OF THE INVENTION

An optically active carboxylic acid of the formula (4):

$$R_1-COS-(CH_2)_n-CH(R_2)-COOH \quad (4)$$

wherein $R_1$ is alkyl, aralkyl or aryl, $R_2$ is alkyl, and n is 1 or 2, is a valuable starting material for the production of various optically active compounds having physiological activities. For example, $D(-)-\beta$-acetylthioisobutyric acid is an important intermediate for the preparation of N-(D-$\alpha$-methyl-$\beta$-mercaptopropionyl)-L-proline which is useful hypotensive agent of angiotensin converting enzyme inhibitor series.

PROBLEMS TO BE SOLVED BY THE INVENTION

Such optically active compounds, however, have hitherto been prepared only by considerably complicated processes since it is difficult to prepare them through the usual chemical synthesis.

The inventors had proposed a method of producing optically active carboxylic acid of the formula(4) by enzymatically asymmetrically hydrolyzing a racemic carboxylic ester of the formula(1):

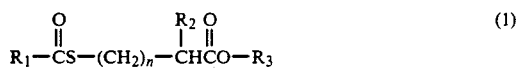

wherein $R_1$, $R_2$ and n are as defined above, and $R_3$ is alkyl(Japanese Patent Appln. LOP-Publn. Nos. 12992/1985 and 12993/1985).

In this process, only one of the optical antipode ester(1) is hydrolyzed and converted into optically active carboxylic acid(4), while the other remains unchanged in the reaction mixture. It would highly be advantageous if the remaining optical antipode of the starting ester of the formula(1) could be racemized to produce the starting racemic ester(1) and recycled. Such racemizing process, however, have never been found hitherto.

The inventors have tried to racemize the optical antipode using various racemization catalysts, for example, strongly acidic compounds such as trichloroacetic acid, trifluoroacetic acid, p-toluenesulfonic acid, concentrated sulfuric acid, etc., strongly basic inorganic compounds such as sodium hydride, sodium hydroxide, etc., alcoholates such as sodium methylate, salts such as sodium acetate, sodium carbonate, etc., with unsuccess.

The inventors have now surprisingly found that an optically active carboxylic acid ester can easily be racemized by contacting it with an amine compound.

SUMMARY OF THE INVENTION

Therefore, the invention relates to a process for racemizing optically active carboxylic acid ester of the formula(1):

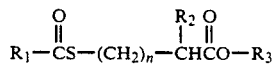

wherein $R_1$ is alkyl, aralkyl or aryl, $R_2$ and $R_3$ independently are alkyl, and n is 1 or 2, which comprises contacting the compound of the formula(1) with an amine compound.

However, the racemization of the present invention proceeds relatively slowly, and the yield is not so high.

Therefore, the inventors have investigated the mechanism of said racemization and found that the optically active carboxylic acid ester is first decomposed in the presence of an amine compound to produce an unsaturated carboxylic acid ester of the formula(2) or (3):

and a thiocarboxylic acid of the formula(5):

and then the thiocarboxylic acid adds to the unsaturated carboxylic acid, thus producing the racemic ester(1). In the above formulas(2), (3) and (5), $R_1$, $R_2$ and $R_3$ have the same meaning as defined above.

In the racemization mechanism as mentioned above, the thiocarboxylic acid and the unsaturated carboxylic acid ester(2) or (3) are continuously eliminated from the optically active carboxylic acid ester(1), and the thiocarboxylic acid is continuously adding to the unsaturated carboxylic acid ester(2) or (3). Namely, said racemization consists of repeated elimination and readdition, and said elimination is assumed to be the rate-limiting stage of the racemization.

The thiocarboxylic acid(5) is relatively unstable and susceptible to decomposition during racemization due to the catalytic action of the amine compound, leading to decrease in the yield and coloration of the reaction mixture. Therefore it is preferable to facilitate the readdition of the thiocarboxylic acid to the unsaturated carboxylic acid ester.

The inventors have also found now that the elimination as mentioned above can be facilitated by the presence of a dipolar aprotic solvent.

Therefore, another aspect of the present invention is to provide a process for racemizing optically active carboxylic acid ester of the formula(1), which comprises contacting said optically active ester(1) with an amine compound in the presence of a dipolar aprotic solvent in order to facilitate the liberation of thiocarboxylic acid from the optically active ester(1).

Further aspect of the invention is to provide a process for racemizing optically active carboxylic acid ester of the formula(1), which comprises contacting said optically active ester(1) with an amine compound in the presence of the unsaturated carboxylic acid ester of the formula(2) when n in the formula(1) is 1, or of the formula(3) when n in the formula(1) is 2, in order to facilitate the readdition of the thiocarboxylic acid.

Still further aspect of the invention is to provide a process for racemizing optically active carboxylic acid ester of the formula(1), which comprises contacting said optically active ester(1) with an amine compound in the presence of both a dipolar aprotic solvent and the unsaturated carboxylic acid ester of the formula(2) or (3).

Suitable $R_2$ in the compound(1) are alkyl of 1–6 carbon atoms, aralkyl of 7–18 carbon atoms, and aryl of 6–14 carbon atoms, preferably methyl, ethyl, benzyl and phenyl.

Suitable $R_2$ which may be mentioned are alkyl of 1–6 carbon atoms. Suitable $R_3$ are alkyl of 1–6 carbon atoms.

Examples of the optically active ester(1) are methyl S-acetyl-β-mercaptoisobutyrate, methyl S-acetyl-γ-mercapto-α-methyl-n-butyrate, methyl S-benzoyl-β-mercaptoisobutyrate, methyl S-phenylacetyl-β-mercaptoisobutyrate, etc.

Any organic amines may be used as an amine compound of the present invention, and tributylamine, monoethanolamine, diethanolamine, triethanolamine, and the like are preferred. Strongly basic tertiary amines are especially preferred. Examples of such preferred amines are DABCO(1,4-diazabicyclo[2.2.2]octane), DBN(1.5-diazabicyclo[4.3.0]nonene-5), and DBU(1.8-diazabicyclo[5.4.0]undecene-7). The above mentioned amine compounds may be used alone or in combinations thereof.

Unsaturated carboxylic acid esters of the formula(2) are, for example, methyl methacrylate, ethyl methacrylate, butyl methacrylate, and methyl 2-ethylacrylate, and the like.

Examples of the unsaturated carboxylic acid ester of the formula(3) are 3-methoxycarbonyl-1-butene, 3-methoxycarbonyl-1-pentene, and 3-ethoxycarbonyl-1-butene.

The reaction of the present invention may preferably be conducted with exclusion of water as much as possible in order to prevent possible hydrolysis of the ester and/or the thioester bond of the compound of the formula(1).

Though it is preferable to perform the present process without any solvent, it may be conducted in an inert aprotic solvent. Suitable solvents are, for example, saturated hydrocarbons such as n-heptane etc., aromatic hydrocarbons such as toluene, xylene, etc.

In the practice of the present process, the racemization is essentially carried out by adding a amine compound to the optically active carboxylic acid ester. Preferably, the present process is carried out in the presence of a dipolar aprotic solvent and/or in the presence of an unsaturated carboxylic acid ester of the formula(2) or (3), as mentioned above. Examples of suitable dipolar aprotic solvents which may be mentioned are N,N-dimethylformamide, dimethyl sulfoxide, hexamethylphosphoric triamide, N-methylpyrrolidone, and the like. The amount of the dipolar aprotic solvents may vary in a wide range and usually from 0.1 to 100 parts, preferably 0.5–10 parts by weight per 1 part of the starting ester(1). The addition of the dipolar aprotic solvent facilitates the elimination of the thiocarboxylic acid from the optically active carboxylic acid ester. The compound(2) is used when n in the ester(1) is 1, and the compound(3) is used when n is 2. The amount of the unsaturated ester(2) or (3) is in the range of 0.1–100 times the molar amount of the optically active starting ester. Polymerization inhibitors such as hydroquinone may also be added in order to prevent polymerization of the unsaturated carboxylic acid esters. The concentration of said polymerization inhibitors in the reaction mixture may be in the range of 0.01–1% by weight.

The preferred amount of the amine compound is not critical and may range from 0.005 to 1 mol per mol of the starting carboxylic acid ester(1).

The reaction temperature is not specifically restricted, but preferably in the range of 50° to 200° C. in order to complete the racemization within a reasonable time.

The racemized carboxylic acid ester may be recovered from the reaction mixture by conventional methods such as distillation, chromatography, and the like.

As mentioned above, the invention provides a process for racemizing an optically active carboxylic acid ester of the formula(1) using an amine compound. In the present process, the yield is higher in comparison with the usual racemization and the product of high quality can be obtained without any coloration.

Thus, the present invention enables to recover and recycle the antipode ester remaining in the reaction mixture of the enzymatic and asymmetric hydrolyzation of the racemic carboxylic acid ester(1).

The invention is further illustrated by the following Examples.

EXAMPLE 1

10 g of methyl L-(+)-S-acetyl-β-mercaptoisobutyrate($[\alpha]D^{25} = +60.2°(c=2.0, CHCl_3)$), 20 g of methyl methacrylate containing 0 2% by weight of hydroquinone, and 500 mg of DBU(1,8-diazabicyclo[5.4.0]undecene-7) were placed in a glass vessel, and the mixture was heated at 100° C. for 5 hours while stirring under $N_2$-atmosphere.

The nature of the reaction mixture before and after the reaction is shown in Table 1. It is clear from Table 1 that the concentration of the ester wa maintained approximately constant level while the positive degree of the specific rotation decreased, indicating that racemization of the (+)ester proceeded. Coloration of the resultant reaction mixture could scarcely been observed.

The reaction mixture was distilled under reduced pressure to give 7.41 g of methyl S-acetyl-β-mercaptoisobutyrate as a distillate(98.1% purity), and the specific rotation$[\alpha]D^{25}$ of it was found to be $+36.6°(c=2, CHCl_3)$.

TABLE 1

|  | Before the reaction | After the reaction |
| --- | --- | --- |
| Concentration of ester ( * ) | 33.3 | 33.0 |
| $[\alpha]_D^{25}$ (**) | +0.199° | +0.111° |

( * ): Concentration (wt. %) of methyl S-acetyl-β-mercaptoisobutyrate in the reaction mixture, determined by HPLC.
( * * ): Determined after 1:10 dilution with $CHCl_3$, in a 10 mm cell, using PM 101 Automatic Polarimeter of Union Giken.

EXAMPLE 2

10 g of methyl L-(+)-S-acetyl-β-mercaptoisobutyrate ($[\alpha]D^{25} = +60.2°(c=2.0, CHCl_3)$), 40 g of methyl methacrylate containing 0.2% by weight of hydroquinone, and 500 mg of DHU(1,8-diazabicyclo[5.4.0]undecene-7) were reacted at 100° C. for 9 hours while stirring under $N_2$-atmosphere. A further amount(500 mg) of DBU wa added and the reaction was continued for additional 11 hours(total 20 hours). The time cource of the concentration of methyl S-acetyl-β-mercaptoisobutyrate and the specific rotation of the reaction mixture are shown in Table 2. From the results it is clear that methyl S-acetyl-β-mercaptoisobutyrate was stable and that racemization proceeded. No coloration of the reaction mixture could be observed.

The reaction mixture was distilled under reduced pressure to give methyl S-acetyl-β-mercapto-isobutyrate having $[\alpha]D^{25}$ of $+9.1°(c=2, CHCl_3)$.

TABLE 2

| Reaction time (hr) | Concentration of ester (*) | Specific rotation of the reaction mixture (**) |
|---|---|---|
| 0 | 20.1 | +0.124° |
| 3 | 19.9 | +0.092° |
| 5 | 19.8 | +0.078° |
| 7 | 20.1 | +0.068° |
| 9 | 19.8 | +0.061° |
| 10 | 19.7 | +0.050° |
| 13 | 19.9 | +0.033° |
| 17 | 19.8 | +0.020° |
| 20 | 19.8 | +0.020° |

(*): Concentration (wt. %) of methyl S-acetyl-β-mercaptoisobutyrate in the reaction mixture, determined by HPLC.
(**): Determined after 1:10 dilution with CHCl₃, in a 10 mm cell, using PM 101 Automatic Polarimeter of Union Giken.

EXAMPLE 3

100 g of methyl L-(+)-S-acetyl-β-mercaptoisobutyrate ($[\alpha]D^{25}= +60.2°(c=2.0, CHCl_3)$) and 6 g of DBU(1,8-diazabicyclo[5.4.0]undecene-7) were placed in a glass vessel, and the mixture was heated while stirring at 100° C. for 5 hour and then at 150° C. for 5 hours.

After the reaction was complete, the reaction mixture was distilled under reduced pressure to give 58.2 g of a distillate which was identified by IR and NMR spectroscopy as racemic methyl S-acetyl-β-mercaptoisobutyrate. $[\alpha]D^{25}= +4.9°(c=2.1, CHCl_3)$, b.p. 80° C./5 mm Hg.

EXAMPLES 4-9

10 g of methyl L-(+)-S-acetyl-βmercaptoisobutyrate($[\alpha]d^{25}= +60.2°(c=2.0, CHCl_3)$), 500 mg of DBU(1,8-diazabicyclo5.4.0undecene-7) and 50 ml of a dipolar aprotic solvent as indicated in Table 3 were placed in a glass vessel, and the mixture was heated while stirring at 120° C. or 80° C. as indicated for 5 hours. The proceed of the reaction was monitored by measuring the specific rotation of the reaction mixture before and after the reaction using PM 101 Automatic Polarimeter of Union Giken. As shown in Table 3, decrease in the specific rotation reveals the occurrence of racemization.

TABLE 3

| Ex. No. | Solvent | Reaction temperature | Specific rotation ($[\alpha]D^{25}$) before | after |
|---|---|---|---|---|
| 4 | DMF | 120° C. | +1.10° | +0.23° |
| 5 | DMF | 80° C. | +1.10° | +0.854° |
| 6 | HMPA | 120° C. | +1.09° | +0.056° |
| 7 | HMPA | 80° C. | +1.09° | +0.58° |
| 8 | NMP | 120° C. | +1.09° | +0.174° |
| 9 | NMP | 80° C. | +1.09° | +0.792° |

DMF: N,N-dimethylformamide
HMPA: hexamethylphosphoric triamide
NMP: N-methylpyrrolidone
Specific rotation was determined in a 100 mm long cell.

EXAMPLES 10-11

50 g of methyl L-(+)-S-acetyl-β-mercaptoisobutyrate($[\alpha]D^{25}= +60.2°(c=2.0, CHCl_3)$), 2.5 g of DBU(1,8-diazabicyclo[5.4.0]undecene-7) and 250 ml of DMF were placed in a glass vessel, and the mixture was heated while stirring at 80° C. or 50° C. for 10 hours. After the reaction was complete, the reaction mixture was distilled to give a distillate the specific rotation($[\alpha]D^{25}(c=2.0, CHCl_3)$) of which was determined. The results are shown in Table 4.

TABLE 4

| Ex. No. | Reaction temperature | Distillate (g) | Specific rotation |
|---|---|---|---|
| 10 | 80° C. | 35.1 | +30.2° |
| 11 | 50° C. | 37.2 | +43.8° |

EXAMPLE 12

A solution of 10 g of methyl L-(+)-S-acetyl-β-mercaptoisobutyrate($[\alpha]D^{25}= +60.2°(c=2.0, CHCl_3)$) in 50 ml of 1:1 mixture of methyl methacrylate and N,N-dimethylformamide was placed in a glass reactor and 100 mg of hydroquinone and 500 mg of DBU(1,8-diazabicyclo[5.4.0]undecene-7) were added. The resultant mixture was heated at 96° C. for 7 hours under $N_2$-atmosphere.

The time cource of the specific rotation of the reaction mixture and the concentration of methyl S-acetyl-β-mercaptoisobutyrate are shown in Table 5. The concentration of methyl S-acetyl-β-mercaptoisobutyrate remained substantially unchanged whereas the specific rotation of the mixture decreased, indicating that racemization proceeded effectively.

The reaction mixture was distilled under reduced pressure to give 5.96 g methyl S-acetyl-β-mercaptoisobutyrate having $[\alpha]D^{25}$ of $+12.1°(c=2.0, CHCl_2)$. Purity 95%.

TABLE 5

| Reaction time (hr) | Specific rotation of the reaction mixture (*) | Concentration of isobutyrate (wt %) (**) |
|---|---|---|
| 0 | +0.122° | 20.0 |
| 1 | +0.060° | 19.12 |
| 3 | +0.037° | 19.56 |
| 5 | +0.030° | 19.67 |
| 7 | +0.028° | 19.98 |

(*): Determined after 1:10 dilution with CHCl₃, in a 10 mm cell, using PM 101 Automatic Polarimeter of Union Giken.
(**): Determined by HPLC.

EXAMPLE 13

The procedure of Example 12 was repeated except for the 2:1 mixture of methyl methacrylate and N,N-dimethylformamide was used and the reaction was continued for 10 hours. The time cource of the reaction is shown in Table 6. It can be found that racemization proceeded effectively.

The reaction mixture was distilled under reduced pressure to give 5.11 g of methyl S-acetyl-β-mercaptoisobutyrate having $[\alpha]D^{25}$ of $+6.57°(c=2.0, CHCl_3)$. Purity 97%.

TABLE 6

| Reaction time (hr) | Specific rotation of the reaction mixture (*) | Concentration of isobutyrate (wt %) (**) |
|---|---|---|
| 0 | +0.125° | 20.0 |
| 1 | +0.055° | 19.24 |

TABLE 6-continued

| Reaction time (hr) | Specific rotation of the reaction mixture (*) | Concentration of isobutyrate (wt %) (**) |
|---|---|---|
| 3 | +0.035° | 20.10 |
| 5 | +0.024° | 19.54 |
| 7 | +0.017° | 19.99 |
| 10 | +0.010° | 19.75 |

(*): Determined after 1:10 dilution with CHCl₃, in a 10 mm cell, using PM 101 Automatic Polarimeter of Union Giken.
(**): Determined by HPLC.

What is claimed is:

1. A process for racemizing an optically active carboxylic acid ester of the formula (1):

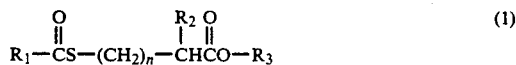

wherein $R_1$ is an alkyl group of 1-6 carbon atoms, an aralkyl group of 7-18 carbon atoms, or an aryl group of 6-14 carbon atoms, $R_2$ and $R_3$ independently are alkyl groups of 1-6 carbon atoms, and n is 1 or 2, which consists of contacting the compound of the formula (1) with an amine compound, wherein said amine compound is selected from the group consisting of monoethanolamine, diethanolamine, and tertiary amine, in the presence of an unsaturated carboxylic acid ester of the formula (2) when n in the formula (1) is 1, and in the presence of an unsaturated carboxylic acid ester of the formula (3) when n in the formula (1) is (2)

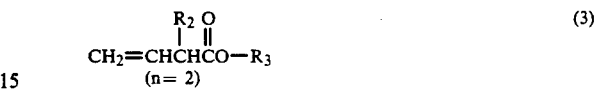

wherein $R_2$ and $R_3$ are as defined above.

2. A process as claimed in claim 1 which is carried out in the presence of a dipolar aprotic solvent.

3. A process as claimed in claim 1 wherein the tertiary amine is selected from the group consisting of 1,4-diazabicyclo[2.2.2]octane, 1,5-diazabicyclo[4.3.0]nonene and 1,8-diazabicyclo[5.4.0]undecene-7.

* * * * *